Oct. 29, 1963 E. S. BOERNER Plant Pat. 2,293
ROSE PLANT
Filed Sept. 24, 1962
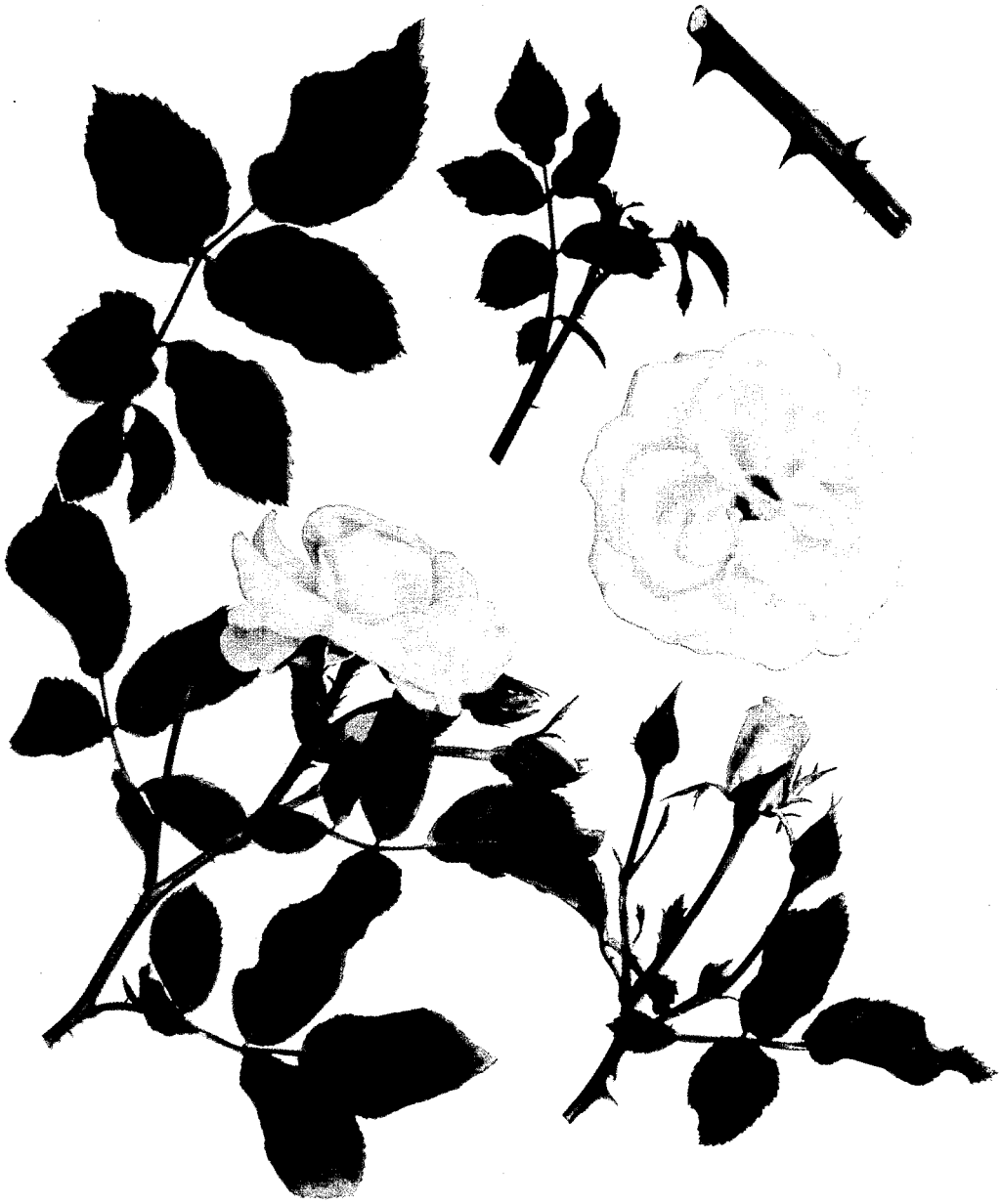
Inventor.
E. S. Boerner
By: Robb & Robb
Attorneys.

United States Patent Office

Plant Pat. 2,293
Patented Oct. 29, 1963

2,293
ROSE PLANT

Eugene S. Boerner, Newark, N.Y., assignor to Jackson & Perkins Company, Newark, N.Y., a corporation of New York Filed Sept. 24, 1962, Ser. No. 225,948
1 Claim. (Cl. Plt.—25)

The present invention relates to a new and distinct variety of rose plant of the floribunda class, which was originated by me by crossing an unnamed and unpatented seedling of "Garnette" (unpatented) with the variety known as "Spartan" (Plant Patent No. 1,357).

The primary objective of this breeding was to improve the flowers of the parent variety "Spartan" by breeding into the same the petal firmness inherent in the flowers of the "Garnette" seedling parent. This objective was fully achieved, along with other desirable improvements, as evidenced by the following unique combination of characteristics which are outstanding in the new variety and which distinguish it from its parents, as well as from all other varieties of which I am aware:

(1) A constantly profuse blooming habit;
(2) A thick and stiff texture of the flower petals;
(3) Cleanliness of the flowers on finishing; and
(4) A distinctive and attractive Scarlet-Red general color tonality of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Garnette."
*Pollen parent.*—"Spartan."
Classification:
*Botanic.*—Floribunda.
*Commercial.*—Floribunda.

*Flower*

(Observations made from specimens grown outdoors at Newark, New York, during the early afternoon, in the latter part of the month of August.)

Blooming Habit: Recurrent—continuous.
Bud:
*Size.*—Medium.
*Form.*—Ovoid; is not affected by wet or hot weather.
*Color.*—When sepals first divided—Spinel Red, Plate 26. When petals begin to unfurl—Spectrum Red, Plate 1. When half-blown: inside of petals—Spectrum Red, Plate 1, very lightly overcast with Scarlet, Plate 1; reverse of petals—Begonia Rose, Plate 1, very lightly overcast with Rose Red, Plate 12.
*Sepals.*—Slightly branched; curl back when petals begin to unfurl. Color: inside—Pale Olivine, Plate 32; outside—Biscay Green Plate 17, lightly overcast with Oxblood Red, Plate 1.
*Calyx.*—Color—Chromium Green, Plate 22. Shape—pear. Size—small. Aspect—smooth. Odor when rubbed—none.
*Peduncle.*—Length—medium. Aspect—smooth. Strength—erect; slender. Color—Madder Brown, Plate 13.
*Opening.*—Opens up well; is not affected by adverse weather conditions.

Bloom:
*Size.*—Medium. Average size when fully expanded—4 inches.
*Borne.*—Several together and in irregular clusters; profuse blooms at all times.
*Stems.*—Medium length; strong.
*Form (when first open).*—Cupped. Permanence—retains its form to the end, but outer petals curl back.
*Petalage.*—Double (full but open center). Number of petals under normal conditions—from 25 to 30.
*Color.*—Center of flower—Spectrum Red, Plate 1, lightly overcast with Scarlet-Red, Plate 1. Outer petals—Scarlet-Red, Plate 1, very lightly overcast with Scarlet, Plate 1. Base of petals (aiglet)—Light Chalcedony Yellow, Plate 17. Inside of petals—Scarlet-Red, Plate 1. Reverse of petals—Rose Red, Plate 12, very lightly overcast with Begonia Rose, Plate 1. General tonality from a distance—Scarlet-Red, Plate 1.
*Discoloration.*—General tonality at end of first day—Scarlet-Red, Plate 1. Second day—Scarlet-Red, Plate 1. Third day—Scarlet-Red, Plate 1, very lightly overcast with Scarlet, Plate 1.

Petals:
*Texture.*—Thick; stiff; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly; finishes very clean.
*Fragrance.*—Moderate. Nature—tea (average hybrid tea scent).
*Lasting quality.*—On the plant—long. As cut flower—long.

*Genital Organs*

Stamens, Anthers: Medium size; many; regularly arranged around styles. Color—Orange-Buff, Plate 3.
Stamens, Filaments (threads): Medium length. Color—Pale Cinnamon Pink, Plate 29.
Pollen: Color—Maize Yellow, Plate 4.
Styles: Bunched; uneven length; medium length; thin.
Stigmas: Color—Buff-Yellow, Plate 4.
Ovaries: All enclosed in calyx.
Hips: None.
Seeds: None.

*Plant*

Form: Bush.
Growth: Vigorous; upright.
Foliage: Compound of 3–7 leaflets.
*Size.*—Medium.
*Quantity.*—Normal.
*Color.*—New foliage: upper side—Victoria Lake, Plate 1; under side—Oxblood Red, Plate 1. Old foliage: upper side—Forest Green, Plate 17; under side—Light Bice Green, Plate 17.
*Shape.*—Oval pointed.
*Texture.*—Upper side—leathery. Under side—smooth.
*Ribs and veins.*—Ordinary.
*Edge.*—Serrated (saw-toothed).
*Serration.*—Both double and single; small.

*Leaf stem.*—Color—Chromium Green, Plate 31. Under side—prickly.

*Stipules.*—Medium length; bearded.

Wood:

*New wood.*—Color—Van Dyke Red, Plate 13. Bark—Smooth.

*Old wood.*—Color—Cress Green, Plate 31. Bark—Smooth.

Thorns:

*Thorns.*—Quantity: on main stalks from base—few; on laterals from stalk—few. Form—narrow base; medium length; straight. Color (when young)—Acajou Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of a constantly profuse blooming habit, thick and stiff flower petal texture, cleanliness of the flowers on finishing, and a distinctive and attractive Scarlet-Red general color tonality of the flowers.

No references cited.